United States Patent [19]

Henry

[11] Patent Number: 5,368,016
[45] Date of Patent: Nov. 29, 1994

[54] AIRWAY ANAESTHESIA

[76] Inventor: Richard A. Henry, 7 Toronto Street, Kingston, Ontario, Canada

[21] Appl. No.: 949,445

[22] Filed: Sep. 22, 1992

[51] Int. Cl.$^5$ ............................................. A61M 16/00
[52] U.S. Cl. .......................... 128/200.23; 128/200.24; 128/202.27; 128/203.12; 128/207.14
[58] Field of Search .................... 128/200.14, 200.23, 128/203.12, 203.15, 203.29, 10–13, 200.24, 202.27, 200.26, 206.29, 207.14; 239/573; 222/154, 156, 402.13, 501, 507

[56] References Cited

U.S. PATENT DOCUMENTS

| 1,498,810 | 6/1924 | Poe | 128/200.26 |
|---|---|---|---|
| 2,564,400 | 8/1951 | Hall | 128/200.14 |
| 3,138,331 | 6/1964 | Kutik | 239/573 |
| 3,323,690 | 6/1967 | Monahon | 222/402.13 |
| 3,998,226 | 12/1976 | Harris | 128/203.15 |
| 4,068,658 | 1/1978 | Berman | 128/200.26 |
| 4,327,721 | 5/1982 | Goldin et al. | 128/207.15 |
| 4,421,249 | 12/1983 | Williamson et al. | 222/154 X |
| 4,432,350 | 2/1984 | Breslau et al. | 128/17 X |
| 4,848,331 | 7/1989 | Northway-Meyer | 128/200.26 |
| 4,969,578 | 11/1990 | Gander et al. | 128/200.23 X |
| 5,060,643 | 10/1991 | Rich et al. | 128/200.23 |
| 5,069,204 | 12/1991 | Smith et al. | 128/203.15 X |
| 5,119,806 | 6/1992 | Palson et al. | 128/200.14 |
| 5,184,761 | 2/1993 | Lee | 128/200.23 X |
| 5,201,308 | 4/1993 | Newhouse | 128/203.15 |

FOREIGN PATENT DOCUMENTS 1166977 4/1964 Germany .......................... 128/200.26

OTHER PUBLICATIONS

Christoforidis et al, *Chest*, 59 (6): 629–633 (1971).
Vuckovic et al, *Anesth. Analg.*, 59(10): 803–804 (1980).
Korttila et al, *Acta Anaesth. Scanda.*, 25: 161–165 (1981).
Kirkpatrick et al, *Am. Rev. Respir. Dis.*, 136: 447–449 (1987).
Isaac et al, *Anaesthesia*, 45: 46–48 (1990).
Foster et al, *Am. Rev. Respir. Dis.*, 146: 520–522 (1992).

*Primary Examiner*—Richard J. Apley
*Assistant Examiner*—Donna L. Maraglio
*Attorney, Agent, or Firm*—Timothy R. Kroboth

[57] ABSTRACT

The present invention provides for improved delivery of anaesthetic to an airway. By the invention, topical airway anaesthesia is passively provided. A method in accordance with the invention, provides for release of a suitable anaesthetic in aerosolized form from a canister containing the anaesthetic, and utilizes an oropharyngeal airway.

9 Claims, 2 Drawing Sheets

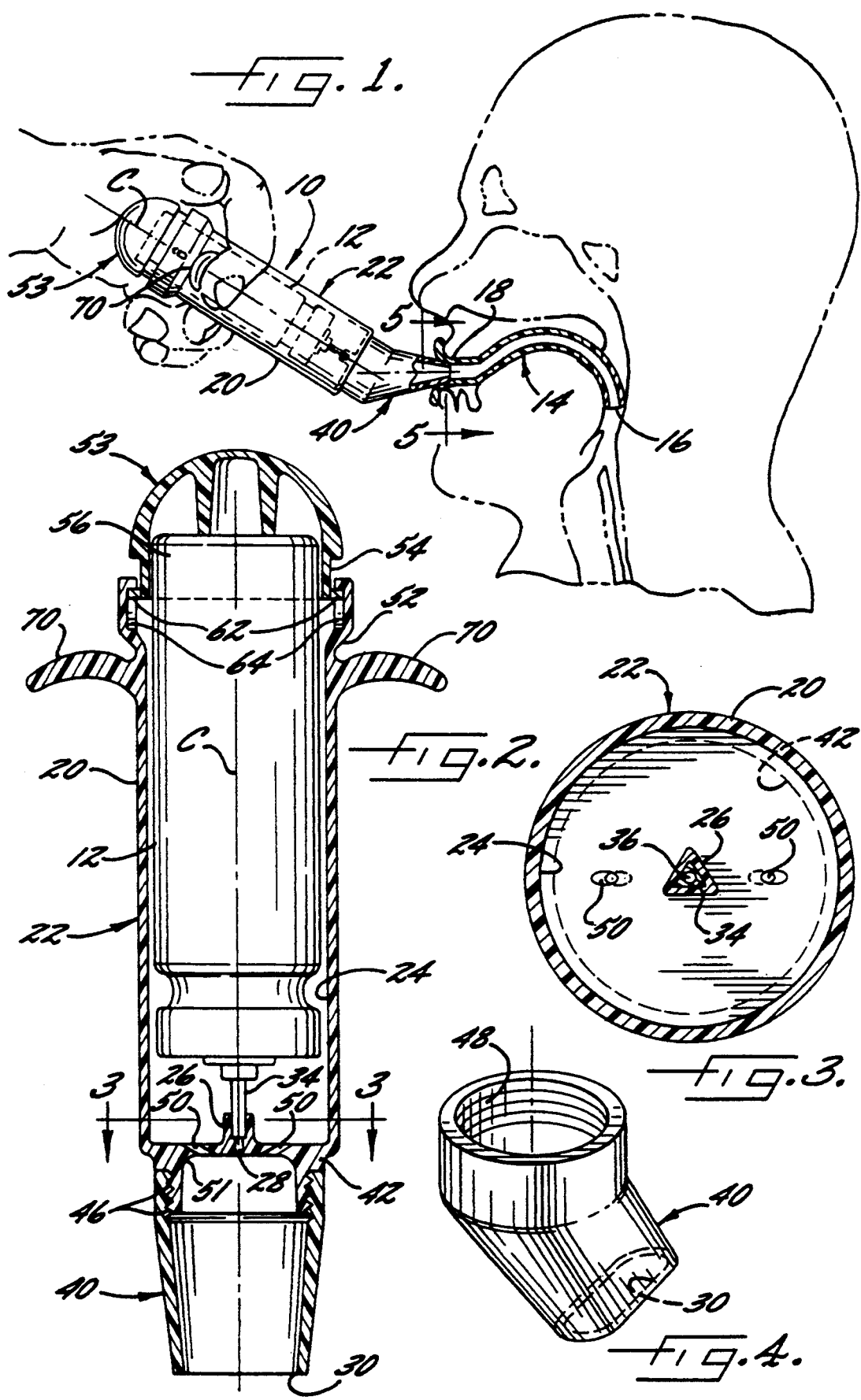

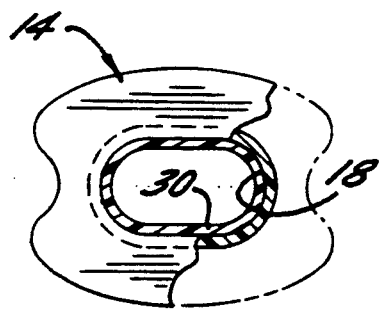
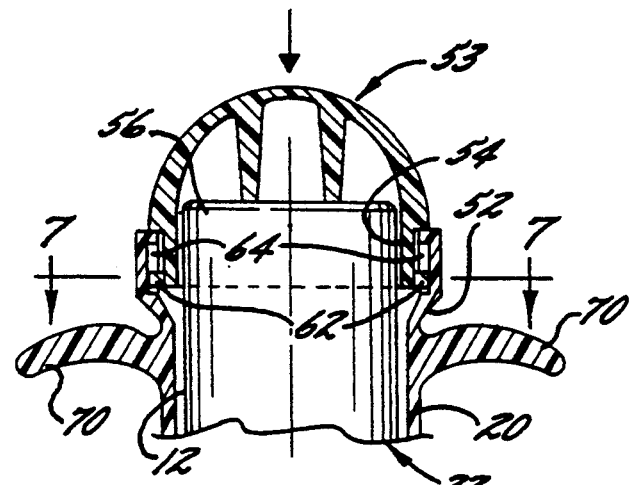
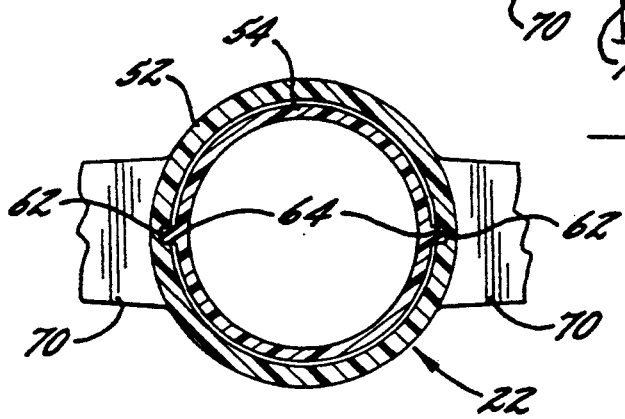

AIRWAY ANAESTHESIA

BACKGROUND OF THE INVENTION

This invention relates to improved delivery of topical local anaesthetic agents to an airway.

Adverse physiological response to laryngoscopy and intubation remains a significant problem of airway manipulation, both during anaesthesia and other diagnostic procedures. Tactile stimulation of receptors in the pharynx, hypopharynx, vocal cords and tracheal mucosa results in reflex gagging, coughing, bucking and laryngospasm as well as release of catecholamine (adrenaline and nor-adrenaline) and direct reflex sympathetic stimulation of the heart.

Clinical manifestations, other than the obvious motor responses, include a rise in pulse rate and blood pressure. These changes can be marked and are usually well tolerated by young healthy patients. However, in the elderly, premature neonates, or patients with cardiac or neurological disease, these haemodynamic changes, with concomitant increase in myocardial work and a decrease in cardiac output, can be critical and overcome the ability of a patient to compensate for existing disease.

Sensory block of the upper airway with an aerosolized, topical anaesthetic such as lidocaine, is possible using an ultrasonic nebulizer, an IPPB device or a compressed gas-powered jet nebulizer, and is clinically effective in blunting these responses. See, for instance, Christoforidis et al, Chest, 59 (6): 629-633 (1971); Vuckovic et al, Anesth. Analg., 59 (10): 803-804 (1980); Korttila et al, Acta Anaesth. Scanda. 25: 161-165 (1981); Kirkpatrick et al, Am. Rev. Respir. Dis., 136:447-449 (1987); Isaac et al, Anaesthesia, 45:46-48 (1990); and Foster et al, Am. Rev. Respir. Dis., 146:520-522 (1992). However, variable dosage loss due to an unsatisfactory delivery method, is disadvantageous. Therefore, there remains a need for an improved method of delivering a topical anaesthetic to a patient's airway.

Moreover, this prior art delivery technique is primarily reserved for procedures in awake patients as it requires patient cooperation, in particular active breathing, and is time consuming. Therefore, there remains a need for an improved method of delivering a topical anaesthetic to the upper airway of an unconscious or uncooperative patient without necessitating direct vision achieved by laryngoscopy.

Topical lidocaine spray currently available from ASTRA as "Xylocaine Endotracheal Aerosol" requires direct application under vision best achieved at laryngoscopy. The laryngoscopy is disadvantageously performed without prior airway topicalization, and intubation carried out at the time of laryngoscopy occurs too soon after the anaesthetic agent is applied for significant benefit to be achieved. The large droplet size of the current aerosol has been implicated in inducing airway irritation and even laryngospasm. Any technique such as spraying the trachea and vocal cords at laryngoscopy, that increases the duration and number of manipulations of the procedure has been shown to increase the stress response.

The Laryngojet technique of instilling liquid lidocaine directly into the trachea just before intubation does have small beneficial effect by blunting the early tracheal response to the tube, but has no effect on the initial response to laryngoscopy and intubation. Bronchodilator aerosol has been administered via the breathing circuit, to a mechanically ventilated patient intubated with an endotracheal tube.

General anaesthetic and induction agent dosages are limited by their adverse effects and must be titrated to a patient's individual requirements in order to achieve the correct depth of anaesthesia without haemodynamic compromise. Titration of the dose and timing of the airway, manipulation, in particular of an intubation, are necessary. A reliable, simple and reproducible method of blocking/blunting the physiological response to intubation would simplify anaesthetic induction and intubation.

Intubating a patient with an anaesthetized airway requires a significantly lighter plane of anaesthesia. The intubation could possibly be achieved safely and reliably under light general anaesthesia without muscle relaxation. Therefore, a method providing for reliable and rapid sensory block of the upper airway, would benefit this aspect of anaesthesia. Such a method would be especially advantageous if it could be used to provide reliable sensory block of the upper airway without direct vision achieved by laryngoscopy.

SUMMARY OF THE INVENTION

It is accordingly an object of the present invention to provide improved delivery of a topical anaesthetic to a patient's airway.

It is a further object to provide improved delivery of a topical anaesthetic to the upper airway of an unconscious or uncooperative patient.

It is a still further object to provide reliable sensory block of the upper airway without direct vision achieved by laryngoscopy.

It is an even further object to rapidly produce effective topical airway anaesthesia.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided a reliable and rapid method for passively providing topical airway anaesthesia. In accordance with the method of this invention, an anaesthetic suitable for topical airway anaesthesia and a suitable aerosol-forming propellant, are provided in a canister adapted to release the anaesthetic in aerosolized form, and disposed within a housing provided with a lid member. Also in accordance with the method, an oropharyngeal airway is inserted into the mouth of a patient according to current standard practice. Thereafter, the anaesthetic in aerosolized form is released from the canister into the oropharyngeal airway, and thence into anaesthetizing contact with the patient's oropharyngeal cavity, by exerting pressure upon the lid member of the housing. The lid member may be transparent in which case the canister may be viewed through the lid member.

A preferred aerosol delivery device for carrying out the method includes a nozzle having an exit orifice adapted for fluid communication with the oropharyngeal airway. Accordingly, the nozzle may be positioned into fluid communication with the oropharyngeal airway. After release of the anesthetic from the canister into the oropharyngeal airway, the nozzle may be separated from fluid communication with the oropharyngeal airway. The preferred delivery device may also include a valve stem seat of unique cross-sectional size and/or shape, and the canister may likewise include a valve stem of complementary cross-sectional size and/or shape.

In the drawing and in the detailed description of the invention that follows, there is shown and essentially described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIG. 1 is a perspective view of a preferred embodiment of an apparatus useful for carrying out the present invention;

FIG. 2 is a detailed cross-sectional view of the aerosol delivery device of FIG. 1, taken substantially along the longitudinal axis thereof;

FIG. 3 is an enlarged, cross-sectional view taken substantially along line 3—3 of FIG. 2;

FIG. 4 is a perspective view of the nozzle the aerosol delivery device of FIG. 1;

FIG. 5 is a partial section taken substantially along line 5—5 of FIG. 1;

FIG. 6 is a cross section of the lid member similar to FIG. 2, but shown in a moved position; and FIG. 7 is a cross section taken substantially along line 7—7 in FIG. 6.

DETAILED DESCRIPTION OF THE INVENTION

As explained above, the present invention passively provides topical airway anaesthesia. In other words, active breathing of a patient is not necessary. Thus, this invention may beneficially be used on both unconscious and awake patients.

Advantageously, this invention may be used to provide reliable sensory block of the upper airway without direct vision of the anesthesiologist. Beneficially, this invention will facilitate smooth induction of anaesthesia by blunting the stress response to intubation. Intubation is routinely performed soon after induction, prior to surgery. A lighter plane of anaesthesia to achieve intubation may result and the need for muscle relaxation may be obviated, thus simplifying this critical period during general anaesthesia.

Superficial sensory block is rapid, typically onsetting within 5 to 30 seconds, with the block becoming more profound over a few minutes and affecting the pressure receptors deeper in the airway mucosal surface. By comparison, a nebulized mist of aerosolized lidocaine, actively breathed, typically takes about ten to fifteen minutes to achieve delivery of the dose requirement with only about 20% of the drug dose delivered to the patient.

Referring to the drawing, a preferred embodiment of an apparatus 10 for carrying out the present invention is shown. With reference particularly to FIG. 1, an aerosol canister 12 containing a suitable topical anaesthetic and propellant, is shown in fluid communication with an oropharyngeal airway 14, depicted as disposed within the oropharyngeal cavity of a patient who is lying down.

As can be understood from the Figure, an oropharyngeal airway extends from the lips to the pharynx, and has a curved shape that fits over the tongue and an orifice 16 that "looks" straight at the larynx and trachea. Accordingly, an oropharyngeal airway may be advantageously used for administration of an anaesthetic to the upper airway, that is, the epiglottis, hypopharynx, larynx and trachea, and may be used for sensory block without direct vision of the anesthesiologist.

An anaesthetic useful in this invention is suitable for topical airway anaesthesia. A preferred topical anaesthetic is lidocaine. Any other local anaesthetic agent may be used.

An appropriate concentration of the anaesthetic within canister 12, depends upon the topical anaesthetic selected. In the case of lidocaine, about 1–10 wt. % lidocaine will typically be selected, providing about 5 to 20 mg per metered dose. For neonates, an appropriate concentration will produce a smaller dose, that is, about 1 to 5 mg of aerosolized lidocaine per metered dose.

By the term "aerosolized" is meant for purposes of this invention, being in the form of minute droplets having typically an average particle size on the order of 6 to 25 microns. Thus, an aerosolized topical anaesthetic having an average particle size of about 16 microns can be expected to be effective for passive topical anaesthesia from the back of the throat to the primary bronchus. By comparison, a large droplet spray having an average particle size in excess of about 50 to 100 microns, would not be useful in the present invention.

The dosage of the aerosolized anaesthetic to be administered, generally depends upon the patient's weight. Improved delivery with reduced "rain-out" may result in reduced dosage requirements from conventional levels of 2 to 5 mg/Kg. The effective dose of aerosolized lidocaine delivered in accordance with the present invention, may thus range from about 0.5 to 2 mg/Kg.

Aerosol propellants are well known. A suitable aerosol propellant will be non-toxic and compatible with the topical anaesthetic selected. Well known aerosol propellants include freon propellants and mixtures of freon propellants such as Freon 12 and Freon 114.

Referring to FIG. 2, a casing or housing 20 of an aerosol delivery device 22 defines a recess 24 in which aerosol canister 12 is disposed, and includes a valve stem seat 26 provided with an aperture 28 that communicates with an exit orifice 30 of the delivery device. The exit orifice is designed for fluid communication with entrance 18, indicated in FIGS. 1 and 5, to airway 14.

Canister 12, generally constructed as is conventional in the aerosol art, has a tubular valve stem or spray head 34. The valve stem is seated within valve stem seat 26, and has an outlet orifice 36 situated for directing an aerosol discharge through aperture 28. Pressing the valve stem inwardly of the canister causes a metered dose of aerosolized anaesthetic to be released from a pre-filled metering chamber (not shown) and to issue from the canister orifice.

With reference to FIG. 3, the valve stem 34 of of a topical anaesthetic-containing canister may be provided with a unique exterior shape, for instance a triangular cross-sectional shape, and the valve stem seat provided with a complementary configuration. In this way, use of the delivery device may be restricted to a topical anaesthetic. Also, this indexed system would prevent adult strength canisters having a valve stem incompatible in exterior shape with a valve stem seat of a neonatal/paediatric aerosol delivery device, from being used in the neonatal/paediatric delivery device and resulting in potential drug overdose.

Referring to FIGS. 2 and 4, a nozzle 40, beneficially held in place by, and removably detachable from, a threaded tip 42 of casing 20, terminates in the exit orifice of the aerosol delivery device. External threads 46 on tip 42, which is conveniently generally circular, and internal threads 48 of nozzle 40 provide for the attachment and detachment. Tip 42 may have a radiused surface 51 inclined toward aperture 28 to assist cleaning.

If desired, the external nozzle threads could be omitted and the nozzle friction fit into place over or inside tip 42, or the nozzle could be an integral, nonremovable part of casing 20. Removability of the nozzle beneficially permits selection of a nozzle of appropriate size and shape as later described, disposal of a nozzle after use, and makes any cleaning of the casing easier.

Within the perimeter of tip 42 and surrounding aperture 28, one or more openings 50 may be formed in the casing. Openings 50 may facilitate aerosol delivery by allowing entrainment of air with the expelled aerosol.

Advantageously, as shown in FIG. 1, the nozzle is shaped to direct the expelled aerosol at an angle with respect to a main or longitudinal axis C of the casing, so as to facilitate operator use in not requiring direct alignment. Likewise, openings 50 may be disposed at an angle with respect to longitudinal axis C to beneficially direct entrained air flow.

With particular reference to FIG. 5, exit orifice 30 of the aerosol delivery device is advantageously provided with a size and shape suitable for fluid communication with entrance 18 to airway 14. To this end, a generally oval shape of an appropriate size that permits insertion of the exit orifice within the entrance to the airway, may be selected. Beneficially, a sealing, snug fit of the nozzle exit orifice within the airway entrance may be provided to prevent positive pressure emanating from the patient, causing dosage loss. The nozzle may taper to a decreased cross-sectional area to allow a tight fit to a range of airway sizes.

Referring particularly to FIG. 6, the canister may be beneficially closed, but not sealed, within the aerosol delivery device by cooperative fit of a movable lid member 53 with casing 20. For this purpose, a canister insert end 52 of the casing may be flared outwardly to accommodate a peripheral wall portion 54 of lid 53, which is positioned over and around an end 56 of the canister. In this manner, peripheral wall portion 54 may be slidingly fitted interior of outwardly flared end 52 of the casing, but yet air flow between wall portion 54 and the casing, to openings 50 may be provided for.

With reference to FIG. 7, posts 62 projecting from wall portion 54 advantageously are in snapengagement with slots 64 in outwardly flared end 52 to prevent the lid from separating from the casing. Elongated slots 64 are provided with a suitable length for the desired travel of posts 62 within the slots, and also may provide for air flow to openings 50.

The casing beneficially includes a handle 70 to be used in conjunction with lid 53, which has an upper surface advantageously generally dome-shaped or rounded for comfort, for facile, one-handed operation of an aerosol delivery device in accordance with the present invention. If desired, the handle may encircle the exterior of the casing, and the lid could likewise be provided with a handle. Conveniently, handle 70 is located near flared out end 52 of the casing.

Beneficially, the canister may be designed to have distinct colors to indicate metered dose strength, differentiating adult from neonatal/paediatric canisters. Consistent with this, lid 50 may be made of transparent material so that the canister may be viewed without removal of the lid.

Administration of an aerosolized topical anaesthetic through airway 14, beneficially provides for reliable and rapid topical anaesthesia of the upper airway, passively and without direct vision of the anesthesiologist. After sensory block, airway 14 may be removed, and various airway manipulations such as endotracheal tube intubation and laryngoscopy, performed without adverse physiological response attributable to airway manipulation. By comparison, I have found that "Xylocaine Endotracheal Aerosol" released into airway 14 does not provide the desired topical anaesthesia, apparently due to failure to exit from airway 14.

Having described the invention in detail and by reference to a preferred embodiment for carrying out the method thereof, it will be apparent that modifications and variations are possible without departing from the scope of the invention defined in the appended claims. Several variants or modifications have been briefly mentioned for purposes of illustration.

I claim:

1. A method for passively providing topical airway anaesthesia to a patient through an oropharyngeal airway, said method comprising:
   providing an anaesthetic suitable for optical airway anaesthesia and a suitable propellant in a canister disposed within a housing, said housing comprising a transparent lid member and means for preventing an incompatible canister from being used with said housing, said means including a valve stem seat of a non-circular, cross-sectional shape, wherein said canister comprises a valve stem of complementary non-circular, cross-sectional shape and indicia for denoting the dosage strength of said anaesthetic;
   viewing said indicia through said transparent lid member for identification of said canister;
   inserting an oropharyngeal airway into the oropharyngeal cavity of a patient; and
   thereafter releasing said anaesthetic from said canister into said oropharyngeal airway, thereby providing anaesthesia to the patient's airway.

2. The method of claim 1, wherein said anaesthetic is lidocaine.

3. The method of claim 1, wherein said housing further comprises a nozzle having an exit orifice adapted for fluid communication with an entrance to said oropharyngeal airway, and wherein said oropharyngeal airway is tubular, has a length that extends to the pharynx, and has a curved shape adapted to fit over the tongue.

4. The method of claim 3, wherein said nozzle is removable from said housing, and wherein said exit orifice is adapted for a sealing, snug fit within said oropharyngeal airway entrance.

5. The method of claim 1, wherein said transparent lid member is movable, and said housing further comprises handle means for cooperating with the movable lid member for exertion of anaesthetic-releasing pressure.

6. The method of claim 1, wherein said lid member is generally dome-shaped.

7. The method of claim 1, further comprising removing said oropharyngeal airway after sensory block has been achieved.

8. The method of claim 1, wherein a metered dose of said anaesthetic is released into said oropharyngeal airway.

9. The method of claim 1, wherein an aerosol delivery end of said housing comprises means for allowing entrainment of air with released anaesthetic.